United States Patent
Pang et al.

(10) Patent No.: US 11,168,361 B2
(45) Date of Patent: Nov. 9, 2021

(54) CHIP, DETECTION SYSTEM AND GENE SEQUENCING METHOD

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Fengchun Pang, Beijing (CN); Peizhi Cai, Beijing (CN); Yue Geng, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 667 days.

(21) Appl. No.: 16/072,923

(22) PCT Filed: Dec. 15, 2017

(86) PCT No.: PCT/CN2017/116431
§ 371 (c)(1),
(2) Date: Jul. 26, 2018

(87) PCT Pub. No.: WO2018/209944
PCT Pub. Date: Nov. 22, 2018

(65) Prior Publication Data
US 2021/0164032 A1    Jun. 3, 2021

(30) Foreign Application Priority Data

May 15, 2017   (CN) .......................... 201710339668.2

(51) Int. Cl.
*C12Q 1/6869* (2018.01)
*C12Q 1/6837* (2018.01)

(52) U.S. Cl.
CPC ......... *C12Q 1/6869* (2013.01); *C12Q 1/6837* (2013.01); *C12Q 2565/607* (2013.01)

(58) Field of Classification Search
CPC .. C12Q 1/6869; C12Q 1/6837; C12Q 1/6874; C12Q 1/68; G02F 1/13718; G01N 27/41
See application file for complete search history.

(56) References Cited

U.S. PATENT DOCUMENTS 9,372,308 B1   6/2016   Saxena et al.
9,391,126 B2 *  7/2016   Kim .................. G02F 1/134363
(Continued)

FOREIGN PATENT DOCUMENTS

CN       1408075 A       4/2003
CN       1538163 A      10/2004
(Continued)

OTHER PUBLICATIONS

Search Report from European Application No. 17892073.2 dated Feb. 3, 2021.
(Continued)

*Primary Examiner* — Narayan K Bhat
(74) *Attorney, Agent, or Firm* — Calfee, Halter & Griswold LLP

(57) ABSTRACT

A chip, a detection system and a gene sequencing method are provided. When the chip is used for gene sequencing, sample genes and reversible terminating nucleotides are added into micropores and matched therein to release hydrogen ions such that a Nernst potential is induced on an ion-sensitive film surface, and a voltage is applied to the transparent electrode layer to generate an electric field, thereby controlling the switching layer to change its state, and then a base type of the genes is determined based on a type of reversible terminating nucleotide corresponding to information of light emitted from the switching layer upon
(Continued)

changes in the state of the switching layer, thereby gene sequencing is achieved.

16 Claims, 4 Drawing Sheets

(56) References Cited

U.S. PATENT DOCUMENTS

| | | |
|---|---|---|
| 2002/0196518 A1 | 12/2002 | Xu et al. |
| 2003/0081162 A1 | 5/2003 | Miller |
| 2004/0209301 A1 | 10/2004 | You et al. |
| 2005/0274612 A1* | 12/2005 | Segawa ............... G01N 33/5438 204/403.01 |
| 2006/0154248 A1 | 7/2006 | McGrew et al. |
| 2006/0166216 A1 | 7/2006 | Nakao et al. |
| 2012/0092576 A1* | 4/2012 | Nose ................... G02F 1/13718 349/33 |
| 2012/0329192 A1* | 12/2012 | Bustillo ................. G01N 27/27 438/49 |
| 2013/0217598 A1* | 8/2013 | Ludwig ............ G01N 33/54373 506/16 |
| 2019/0025242 A1 | 1/2019 | Pang et al. |

FOREIGN PATENT DOCUMENTS

| | | |
|---|---|---|
| CN | 1816744 A | 8/2006 |
| CN | 1993617 A | 7/2007 |
| CN | 106497774 A | 3/2017 |
| CN | 107118954 A | 9/2017 |
| CN | 107118960 A | 9/2017 |

OTHER PUBLICATIONS

Search Report for International Application No. PCT/CN2017/116431 dated Mar. 14, 2018.
First Office Action for Chinese Patent Application No. 201710339668.2 dated Jan. 30, 2019.

* cited by examiner

CHIP, DETECTION SYSTEM AND GENE SEQUENCING METHOD

RELATED APPLICATION

The present application is the U.S. national phase entry of PCT/CN2017/116431, with an international filling date of Dec. 15, 2017, which claims the benefit of Chinese Patent Application No. 201710339668.2, filed on May 15, 2017, the entire disclosures of both are incorporated herein by reference.

TECHNICAL FIELD

This disclosure relates to the field of detection technologies, and in particular to a chip, a detection system and a gene sequencing method.

BACKGROUND

Gene sequencing techniques are the most commonly used techniques in modern biological studies, and considerable progress has been made in gene sequencing techniques since 1977 when the first generation gene sequencing was developed. The development of gene sequencing techniques includes Sanger sequencing techniques and high-throughput sequencing techniques.

The high-throughput sequencing techniques mainly comprise Illumina's sequencing-by-synthesis, Thermo Fisher's ionic-semiconductor sequencing and connection sequencing and Roche's pyrosequencing. Illumina's sequencing-by-synthesis and Thermo Fisher's connection sequencing both require fluorescent labeling in addition to a laser light source and an optical system, which complicates the sequencing process and increases sequencing time and cost. In contrast, Roche's pyrosequencing does not require a laser light source or an optical system, but it still needs fluorescent labeling. While a sequencing device used in ionic-semiconductor sequencing requires fabricating an ionic sensor and two field effect transistors by a semiconductor process, which involves complicated fabrication processes and a difficult fabrication procedure.

SUMMARY

The embodiments of this disclosure provide a chip, a detection system and a gene sequencing method.

An embodiment of this disclosure provides a chip, comprising: an upper substrate and a lower substrate arranged oppositely, a transparent electrode layer attached to the lower substrate, and a switching layer between the lower substrate and the upper substrate. A plurality of micropores insulated from each other are provided on a surface of the upper substrate facing away from the lower substrate, each micropore having an ion-sensitive film on a bottom thereof, the switching layer is configured for switching between a first state and a second state responsive to an electric field generated between the ion-sensitive film and the transparent electrode layer.

In some embodiments, the switching layer comprises a bistable cholesteric liquid crystal layer, and the chip further comprises a first alignment film and a second alignment film, the first alignment film is located on a surface of the lower substrate facing the upper substrate, the second alignment film is located on a surface of the upper substrate facing the lower substrate.

Furthermore, in some embodiments, the first state comprises a planar state and the second state comprises a focal conic state.

In some embodiments, the switching layer comprises an electrochromic layer, the electrochromic layer exhibiting different colors in the first state and the second state.

In some embodiments, the plurality of micropores are arranged in a matrix on the surface of the upper substrate facing away from the lower substrate.

In some embodiments, a material of the ion-sensitive film is $Si_3N_4$.

In some embodiments, the lower substrate is transparent, and the chip further comprises a black base layer located on a surface of the lower substrate facing away from the upper substrate.

Another embodiment of this disclosure provides a detection system, comprising the chip according to any of the above embodiments.

In some embodiments, the detection system further comprises an optical sensor, the optical sensor being configured for acquiring information of light emitted from the switching layer in different states, the information comprising at least one of light intensity and light color.

Further, the optical sensor comprises an image sensor.

In some embodiments, the chip further comprises a black base layer located on a surface of the lower substrate facing away from the upper substrate.

Yet another embodiment of this disclosure provides a gene sequencing method based on the detection system according to the above embodiments, the method comprising steps of: adding a magnetic bead including a plurality of sample genes enriched by amplification into the micropores of the chip, adding into the micropores four types of reversible terminating nucleotides successively, every time each reversible terminating nucleotide is added, applying a voltage signal to the transparent electrode layer of the chip and sequentially acquiring information of light emitted from the switching layer after the reversible terminating nucleotides are added, and determining a sequence of the sample genes based on the reversible terminating nucleotides corresponding to changes in the information of light emitted from the switching layer.

In some embodiments, determining a sequence of the sample genes based on the reversible terminating nucleotides corresponding to changes in the information of light emitted from the switching layer comprises: recording a type of the reversible terminating nucleotide when the information of light emitted from the switching layer is determined to have changed, and determining the sequence of the sample genes based on the recorded type of reversible terminating nucleotide.

In some embodiments, the chip further comprises a black base layer located on a surface of the lower substrate facing away from the upper substrate, the lower substrate being transparent, wherein recording a type of the reversible terminating nucleotide when the information of light emitted from the switching layer is determined to have changed comprises recording the type of reversible terminating nucleotide when the black base layer is observed through the upper substrate.

In some embodiments, the gene sequencing method further comprises: every time a base type in the sequence of the sample genes is determined, cleaning away the reversible terminating nucleotides added into the micropores and adding a sulfhydryl agent into the micropores.

In some embodiments, the gene sequencing method further comprises: after the base type in the sequence of the sample genes is determined, stopping applying the voltage signal to the transparent electrode layer.

DETAILED DESCRIPTION OF EMBODIMENTS

Specific implementations of the chip, the detection system and the gene sequencing method provided in the embodiments of this disclosure will be described below in detail with reference to the drawings.

Figure 1:
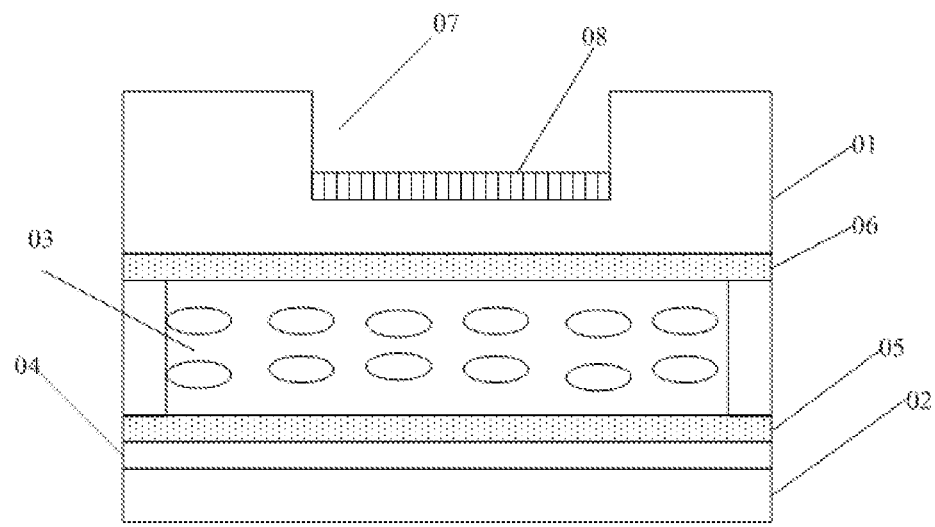
FIG. 1 is a schematic view of a chip provided in an embodiment of this disclosure.

An embodiment of this disclosure provides a chip, which comprises as shown in FIG. 1: an upper substrate 01 and a lower substrate 02 arranged oppositely, a transparent electrode layer 04 and a switching layer 03 located between the lower substrate 02 and the upper substrate 01. The transparent electrode layer 04 is attached to the lower substrate 02. As shown in FIG. 1, the transparent electrode layer 04 is located on a surface of the lower substrate 02 facing the upper substrate 01, and in other embodiments, the transparent electrode layer can be located on a surface of the lower substrate facing away from the upper substrate. A plurality of micropores 07 insulated from each other are provided on a surface of the upper substrate 01 facing away from the lower substrate 02, the micropores 07 having an ion-sensitive film 08 on a bottom thereof. The switching layer 03 is configured for switching between a first state and a second state responsive to an electric field generated between the ion-sensitive film 08 and the transparent electrode layer 04.

The chip provided in the embodiments of this disclosure comprises an ion-sensitive film surface, it can be used in different application scenes. For example, it can be used for gene sequencing. Specifically, sample genes and reversible terminating nucleotides are added into the micropores and matched in the micropores to release hydrogen ions, such that a Nernst potential is induced on a surface of the ion-sensitive film. A material of the ion-sensitive film may include $Si_3N_4$. Therefore, by applying a voltage to the transparent electrode layer attached to the lower substrate to generate an electric field, the state of the switching layer can be changed, for example, switch between the first state and the second state. In this way, the type of reversible terminating nucleotide corresponding to a change in the state of the switching layer can be acquired, and gene sequencing can be achieved based on the type of reversible terminating nucleotide. The chip has a simple structure and low fabrication cost, and the reversible terminating nucleotides for matching and sequencing do not require fluorescent labeling, and optical systems such as a backlight source and a laser light source are not necessary, but instead, gene sequencing can be performed simply by means of reflection of natural light, so the sequencing method is simple and easy to carry out, which greatly reduces the cost and time for gene sequencing.

It should be understood that the chip provided in the embodiment of this disclosure can be applied in any suitable field to carry out a detection function as long as ions can be released during the detection to induce a Nernst potential on the ion-sensitive film surface of the chip.

In specific implementation, in the chip provided in the embodiment of this disclosure, the plurality of micropores on a surface of the upper substrate facing away from the lower substrate can be arranged in a matrix, or in other ways upon actual needs, which will not be limited herein. In an embodiment, the micropores can have an aperture of 1~30 μm.

In the chip provided in an embodiment of this disclosure, as shown in FIG. 1, the switching layer 03 comprises a bistable cholesteric liquid crystal layer, and the chip may further comprise a first alignment film 05 and a second alignment film 06, the first alignment film 05 is located on a surface of the lower substrate 02 facing the upper substrate 01, the second alignment film 06 is located on a surface of the upper substrate 01 facing the lower substrate 02. The liquid crystal layer can be deflected under the effect of the electric field mentioned above, thereby achieving switching between the first state and the second state. Specifically, the bistable cholesteric liquid crystal can be switched from a reflective state (a planar state) to a focal conic state under the effect of the electric field.

Figure 2A:
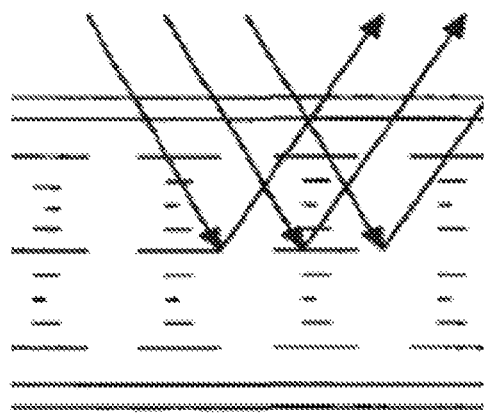
FIG. 2A is a schematic view showing deflection states of bistable cholesteric liquid crystals in the chip provided in the embodiment of this disclosure.
Figure 2B:
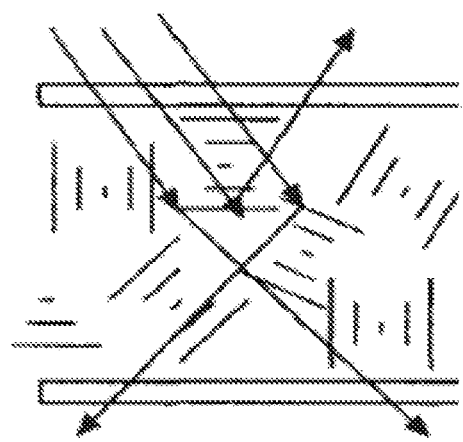
FIG. 2B is a schematic view showing deflection states of bistable cholesteric liquid crystals in the chip provided in the embodiment of this disclosure.
Figure 2C:
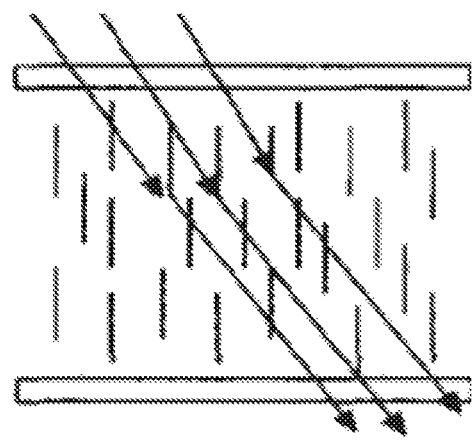
FIG. 2C is a schematic view showing deflection states of bistable cholesteric liquid crystals in the chip provided in the embodiment of this disclosure.

The bistable cholesteric liquid crystal can have three states specifically as shown in FIGS. 2A-2C:

1. A planar state (P state): as shown in FIG. 2A, liquid crystal molecules are arranged spirally in the space around a spiral axis perpendicular to a substrate surface, and when light is incident on the liquid crystal surface, the liquid crystal molecules reflect light having a specific wavelength $\lambda$: $\lambda=np$; wherein $\lambda$ is referred to as a central reflection wavelength, p is a pitch of the liquid crystal material, n is an average refractive index and equal to $(ne+no)/2$, wherein no refers to a normal refractive index and ne refers to an abnormal refractive index. Therefore, the reflection wavelength $\lambda$ can be controlled by the pitch p. The planar state can also be called a reflective state.

2. A focal conic state (FC state): as shown in FIG. 2B, the liquid crystal molecules are still arranges spirally, but the directions of the spiral axes in the liquid crystal domains are randomly distributed and the liquid crystal molecules exhibit a multi-domain state. Incident light is scattered at interfaces of adjacent liquid crystal domains due to sharp changes in the refractive index. As compared with the planar state, light of a same wavelength component emitted from the bistable cholesteric liquid crystals (the switching layer) has a reduced intensity.

3. A homeotropic state (H state): as shown in FIG. 2C, the spiral structures of the liquid crystal molecules are de-spiralized and exhibit a nematic homeotropic alignment, and the liquid crystal layer is a medium of homogeneous refractive index, so it exhibits a transmissive state, and hence the liquid crystal cell exhibits a transparent state.

Figure 3:
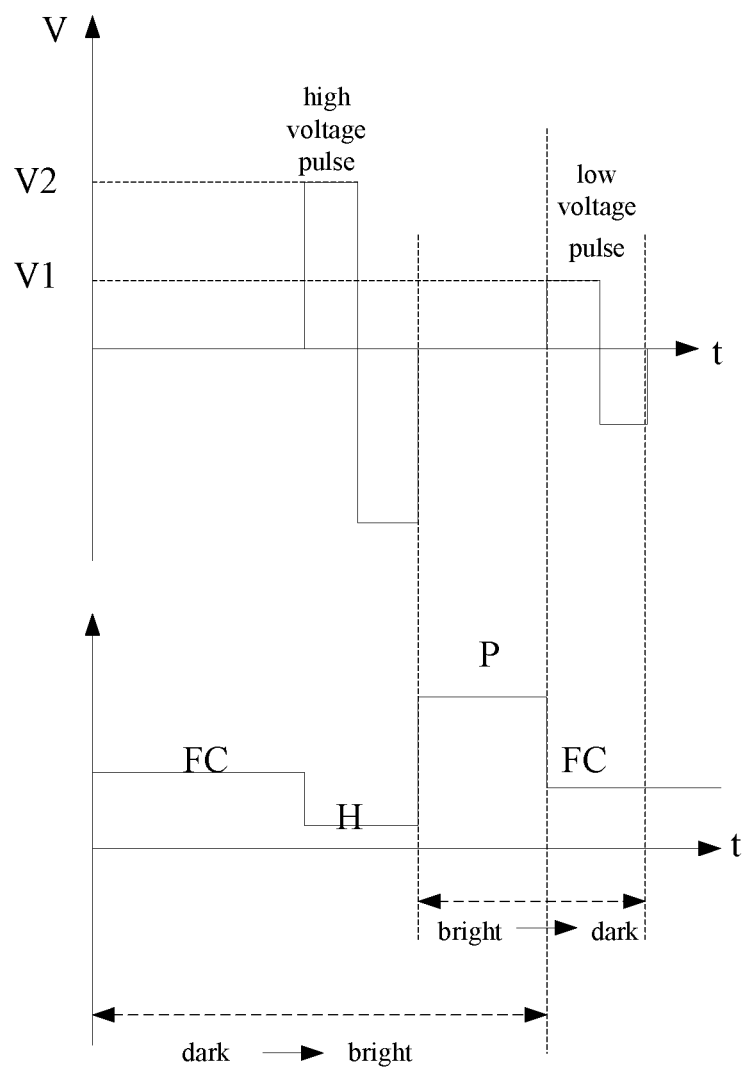
FIG. 3 schematically shows a state switch of the bistable cholesteric liquid crystals provided in an embodiment of this disclosure and a voltage signal applied thereto.

As shown in FIG. 3, an example for the driving the bistable cholesteric liquid crystals is shown schematically. If the cholesteric liquid crystals are initially in a P state, when the voltage is increased from zero to a threshold voltage V1, they will transition from the P state to a FC state, and if the voltage drops from V1 to zero, the cholesteric liquid crystals will return to the P state. If the external voltage across the bistable cholesteric liquid crystals is further increased to a saturation voltage V2 from the value at the FC state, the bistable cholesteric liquid crystals will transition from the FC state to an H state, which is not a stable state. If the voltage rapidly drops to zero, the liquid crystals relax to the P state, i.e., they transition from a dark state to a bright state; if the voltage slowly drops to zero, the liquid crystal molecules will return to the FC state. The P state and the FC state are both stable states, and by changing the external electric field, switching between the two states, i.e., switching between the planar state and the focal conic state, can be achieved. The chip in the embodiments of this disclosure can achieve gene sequencing by acquiring differences in information of light displayed by the bistable liquid crystals in different stable states based on the driving principles of bistable cholesteric liquid crystals.

In other embodiments, the switching layer of the chip can be an electrochromic layer. Specifically, the electrochromic layer can exhibit different colors under the effect of the electric field. Therefore, during gene sequencing, if the sample genes and the reversible terminating nucleotides are matched to release hydrogen ions, a Nernst potential will be induced on the ion-sensitive film surface. A voltage can be applied to the transparent electrode layer attached to the lower substrate to generate an electric field, thereby controlling the electrochromic layer to change its color state, for example, as compared with a normal state with no electric field, the electrochromic layer changes its color under the effect of the electric field between the transparent electrode layer and the ion-sensitive film, and then a base type of the gene is determined in accordance with a type of reversible terminating nucleotides corresponding to a change in the color of the electrochromic layer, and thereby gene sequencing is achieved.

Figure 4:
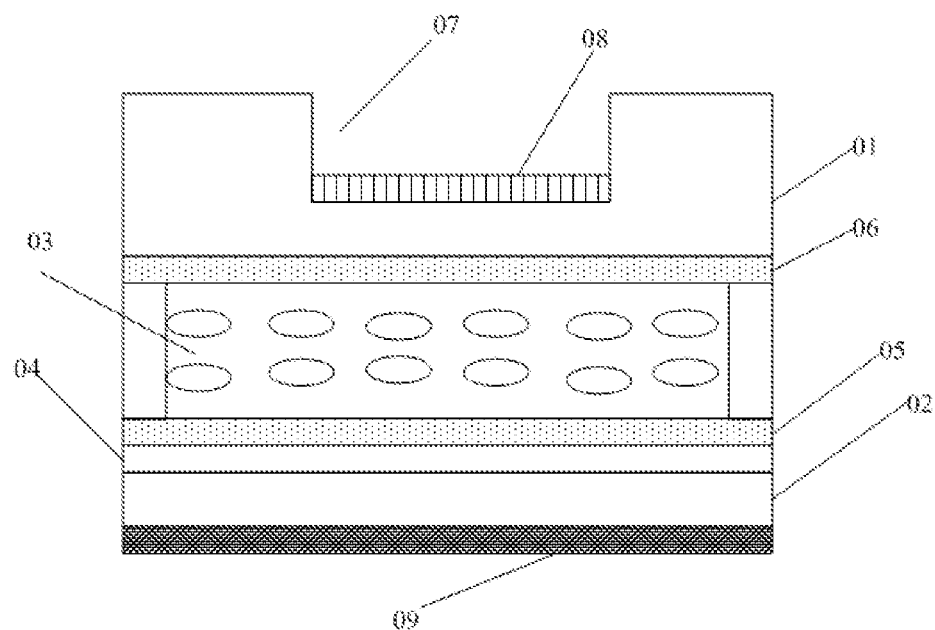
FIG. 4 is a schematic view of a chip provided in another embodiment of this disclosure.

The chip provided in another embodiment of this disclosure further comprises as shown in FIG. 4, a black base layer 09, the black base layer 09 is located on a surface of the lower substrate 02 facing away from the upper substrate 01, and now the lower substrate 02 is be a transparent layer. Arranging a black base layer on a surface of the lower substrate facing away from the upper substrate can facilitate acquisition of changes in state of the switching layer. For example, in an embodiment in which the switching layer is bistable cholesteric liquid crystals, during the gene sequencing, when the sample genes and the reversible terminating nucleotides are matched and synthesized, a potential is induced on the ion-sensitive film, which generates an electric field together with the transparent electrode layer such that the liquid crystals are deflected to form a focal conic state. Due to the absorption of light by the black base layer, human eyes can identify an obvious darkening or a dark state of the surface of the upper substrate of the chip, i.e., the presence of the black base layer may probably be observed through the upper substrate of the chip. When the bistable cholesteric liquid crystals are in a planar state, since the light is almost reflected by the bistable cholesteric liquid crystals, human eyes substantially cannot perceive the black base layer. In light of that, it can be easily determined whether the sample genes and the reversible terminating nucleotides are matched and synthesized. The color of the base layer is not limited to black, and a base layer of other colors is also possible, as long as its color is different from the color exhibited by the switching layer when the switching layer is not subjected to the effect of the electric field.

In some embodiments, the reversible terminating nucleotides for matching with the sample genes for sequencing comprise four different types of reversible terminating nucleotides. Specifically, in contrast with an ordinary nucleotide, an azide group is connected with a 3' terminal of the reversible terminating nucleotide, and a phosphodiester bond cannot be formed during the synthesis of DNA, thereby interrupting the synthesis of DNA. If the reversible terminating nucleotides and the sample genes in the micropores are matched in a complementary manner, the reversible terminating nucleotides is synthesized into the sample gene molecules to release hydrogen ions, and thus a Nernst potential will be induced on the ion-sensitive film surface. By applying a voltage signal to the transparent electrode layer attached to the lower substrate, the bistable liquid crystals can transition from a planar state to a focal conic state.

Based on a same inventive concept, an embodiment of this disclosure provides a detection system, comprising the chip provided in the embodiments of this disclosure.

In some embodiments, the detection system further comprises an optical sensor, and the optical sensor is configured for acquiring information of light emitted from the switching layer in different states, the information comprising at least one of light intensity and light color. In some embodiments, the optical sensor comprises an image sensor for acquiring information of light emitted from the switching layer, thereby achieving gene sequencing. Since the principle of the detection system for solving problems is similar to that of the chip, for the implementation of the detection system, the implementation of the chip can be referred to, which will not be repeated for simplicity.

Figure 5:
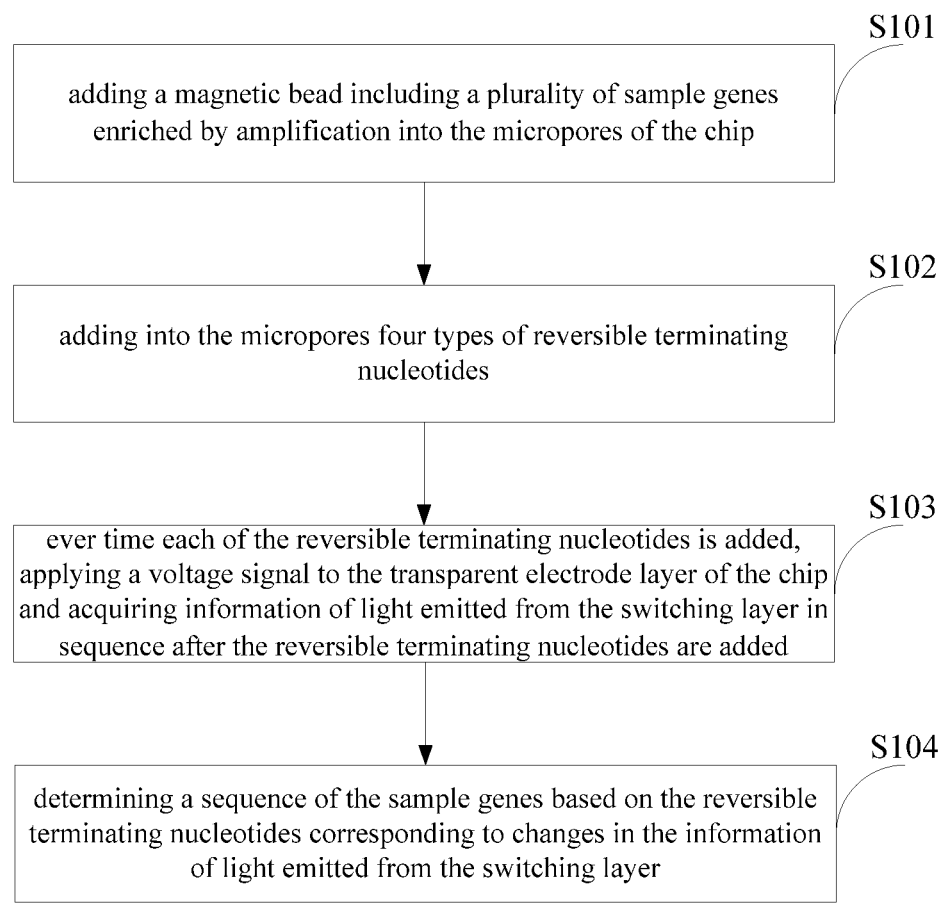
FIG. 5 is a flow chart of a gene sequencing method provided in an embodiment of this disclosure.

Based on a same inventive concept, a further embodiment of this disclosure provides a gene sequencing method based on the detection system provided in the embodiments of this disclosure, which, as shown in FIG. 5, can comprise the following steps.

S101, adding a magnetic bead including a plurality of sample genes enriched by amplification into the micropores of the chip;

S102, adding into the micropores four types of reversible terminating nucleotides;

S103, every time each of the reversible terminating nucleotides is added, applying a voltage signal to the transparent electrode layer of the chip and acquiring information of light emitted from the switching layer in sequence after the reversible terminating nucleotides are added;

S104, determining a sequence of the sample genes based on the reversible terminating nucleotides corresponding to changes in the information of light emitted from the switching layer.

In the gene sequencing method provided in the embodiment of this disclosure, sample genes and reversible terminating nucleotides are added into micropores, where they are matched to release hydrogen ions such that a Nernst potential is induced on an ion-sensitive film surface, and a voltage can be applied to the transparent electrode layer attached to the lower substrate to generate an electric field, thereby controlling the switching layer to switch to a focal conic state, and then a base type of the genes can be determined based on a type of reversible terminating nucleotides corresponding to information of light emitted from the switching layer in the focal conic state, and thereby gene sequencing is achieved. The reversible terminating nucleotides for matching and sequencing used in the gene sequencing method require no fluorescent labeling, and optical systems such as a backlight source and a laser light source are also not required, but instead, gene sequencing is achieved simply by means of reflection of natural light, so the sequencing method is simple and easy to carry out, which greatly reduces the cost and time for gene sequencing.

In some embodiments, step S104 in the gene sequencing method specifically comprises the following steps: recording a type of the added reversible terminating nucleotides when the information of light emitted from the switching layer is determined to have changed; and determining a sequence of the sample genes in accordance with the recorded type of reversible terminating nucleotides. Specifically, when a type of reversible terminating nucleotides is added, from the information of light emitted from the switching layer, it can be determined whether the reversible terminating nucleotides are matched with the sample genes. That is, upon detection of information of light reflected from the lower substrate under the switching layer, it can be determined that the reversible terminating nucleotides are matched with the sample genes; otherwise, it means the reversible terminating nucleotides are not matched with the sample genes (in this case, the switching layer reflects light of other specific wavelengths), and thereby gene sequencing is achieved.

In another embodiment, the chip of the detection system further comprises a black base layer located on a surface of the lower substrate facing away from the upper substrate, and the lower substrate is transparent. Recording a type of the added reversible terminating nucleotide when the information of light emitted from the switching layer is determined to have changed comprises: recording a type of the added reversible terminating nucleotide when the black base layer is observed through the upper substrate. In this embodiment, if the reversible terminating nucleotides are matched with the sample genes, human eyes can easily observe the color of the black base layer through the upper substrate. Accordingly, it can be determined without an optical sensor that the reversible terminating nucleotides are matched with the sample genes.

In yet another embodiment, the gene sequencing method further comprises: every time a base type of the sample genes sequence is determined, cleaning away the reversible terminating nucleotides added into the micropores and adding a sulfhydryl agent into the micropores. In particular, after a type of the nucleotide polymerized in a base position of each sample genes sequence is acquired, a sulfhydryl agent is added to perform chemical cleavage to groups of the reversible terminating nucleotide so as to break the azide group and resume the viscidity at the 3' hydroxyl terminal. That is, a hydroxyl is formed in the original position, which allows continuous polymerization to a second nucleotide so as to perform base type detection in a subsequent position.

The gene sequencing method provided in yet another embodiment of this disclosure further comprises: every time a base type in the sample genes sequence is determined, stopping applying the voltage signal to the transparent electrode layer. This enables the switching layer to resume to the reflective state timely, prevents the switching layer from failing to resume to the reflective state because of the electric field and thus avoids influencing the determining of a next base type.

The embodiments of this disclosure provide a chip, a detection system and a gene sequencing method. The chip comprises an upper substrate and a lower substrate arranged oppositely, a transparent electrode layer and a switching layer located between the lower substrate and the upper substrate. The transparent electrode layer is attached to the lower substrate. A plurality of micropores insulated from each other are provided on a surface of the upper substrate facing away from the lower substrate, the micropores having an ion-sensitive film on a bottom thereof. The switching layer can switch between a first state and a second state responsive to an electric field generated between the ion-sensitive film and the transparent electrode layer. In this way, when the chip is used for gene sequencing, sample genes and reversible terminating nucleotides are matched in the micropores to release hydrogen ions such that a Nernst potential is induced on an ion-sensitive film surface, and an electric field is generated by using the transparent electrode layer to control the switching layer to change its state, and then a base type of the genes is determined in accordance with a type of reversible terminating nucleotides corresponding to information of light emitted from the switching layer upon changes in the state of the switching layer, and thereby gene sequencing is achieved. The chip has a simple structure and low fabrication cost, and the reversible terminating nucleotides for matching and sequencing require no fluorescent labeling, and optical systems such as a backlight source and a laser light source are unnecessary, but instead, gene sequencing can be achieved simply by means of reflection of natural light, so the sequencing method is simple and easy to carry out, which greatly reduces the cost and time for gene sequencing.

Obviously, those skilled in the art can make various modifications and variations to this disclosure without departing from spirits and scopes of the invention. Thus if these modifications and variations to this disclosure fall within the scopes of the claims and the equivalences thereof, this disclosure is intended to include them too.

The invention claimed is:

1. A chip comprising:
an upper substrate and a lower substrate arranged oppositely,
a transparent electrode layer attached to the lower substrate, and
a switching layer between the lower substrate and the upper substrate,
wherein a plurality of micropores insulated from each other are provided on a surface of the upper substrate facing away from the lower substrate, each micropore having an ion-sensitive film on a bottom thereof, wherein the switching layer is configured for switching between a first state and a second state responsive to an electric field generated between the ion-sensitive film and the transparent electrode layer.

2. The chip according to claim 1, wherein the switching layer comprises a bistable cholesteric liquid crystal layer, and the chip further comprises a first alignment film and a second alignment film, wherein the first alignment film is located on a surface of the lower substrate facing the upper substrate, and the second alignment film is located on a surface of the upper substrate facing the lower substrate.

3. The chip according to claim 2, wherein the first state comprises a planar state and the second state comprises a focal conic state.

4. The chip according to claim 1, wherein the switching layer comprises an electrochromic layer, the electrochromic layer exhibiting different colors in the first state and the second state.

5. The chip according to claim 1, wherein the plurality of micropores are arranged in a matrix on the surface of the upper substrate facing away from the lower substrate.

6. The chip according to claim 1, wherein a material of the ion-sensitive film is $Si_3N_4$.

7. The chip according to claim 1, wherein the lower substrate is transparent, and the chip further comprises a black base layer located on a surface of the lower substrate facing away from the upper substrate.

8. A detection system comprising the chip according to claim 1.

9. The detection system according to claim 8, wherein the detection system further comprises an optical sensor, and the optical sensor is configured for acquiring information of light emitted from the switching layer in different states, the information comprising at least one of light intensity and light color.

10. The detection system according to claim 9, wherein the optical sensor comprises an image sensor.

11. The detection system according to claim 8, wherein the chip further comprises a black base layer located on a surface of the lower substrate facing away from the upper substrate.

12. A gene sequencing method based on the detection system according to claim 8, wherein the method comprises steps of:
- adding a magnetic bead including a plurality of sample genes enriched by amplification into the micropores of the chip,
- adding into the micropores four types of reversible terminating nucleotides successively, ion
- every time each reversible terminating nucleotide is added, applying a voltage signal to the transparent electrode layer of the chip and sequentially acquiring information of light emitted from the switching layer after the reversible terminating nucleotides are added, and
- determining a sequence of the sample genes based on the reversible terminating nucleotides corresponding to changes in the information of light emitted from the switching layer.

13. The method according to claim 12, wherein determining a sequence of the sample genes based on the reversible terminating nucleotides corresponding to changes in the information of light emitted from the switching layer comprises:
- recording a type of the reversible terminating nucleotide when the information of light emitted from the switching layer is determined to have changed, and
- determining the sequence of the sample genes based on the recorded type of reversible terminating nucleotide.

14. The method according to claim 13, wherein the chip further comprises a black base layer located on a surface of the lower substrate facing away from the upper substrate, the lower substrate being transparent, wherein recording a type of the reversible terminating nucleotide when the information of light emitted from the switching layer is determined to have changed comprises:
- recording the type of reversible terminating nucleotide when the black base layer is observed through the upper substrate.

15. The method according to claim 12, further comprising:
- every time a base type in the sequence of the sample genes is determined, cleaning away the reversible terminating nucleotides added into the micropores and adding a sulfhydryl agent into the micropores.

16. The method according to claim 15, further comprising:
- after the base type in the sequence of the sample genes is determined, stopping applying the voltage signal to the transparent electrode layer.

* * * * *